US009839789B2

(12) United States Patent
Kozin et al.

(10) Patent No.: US 9,839,789 B2
(45) Date of Patent: Dec. 12, 2017

(54) DEFIBRILLATOR PADDLES WITH LIGHTED SHOCK BUTTONS

(75) Inventors: Simon Edward Kozin, Medford, MA (US); Anthony Matheson, Bedford, MA (US); Constance F. Matheson, legal representative, Bedford, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 513 days.

(21) Appl. No.: 13/981,712

(22) PCT Filed: Jan. 24, 2012

(86) PCT No.: PCT/IB2012/050318
§ 371 (c)(1),
(2), (4) Date: Jul. 25, 2013

(87) PCT Pub. No.: WO2012/101573
PCT Pub. Date: Aug. 2, 2012

(65) Prior Publication Data
US 2014/0005737 A1    Jan. 2, 2014

Related U.S. Application Data

(60) Provisional application No. 61/436,668, filed on Jan. 27, 2011.

(51) Int. Cl.
*A61N 1/39*     (2006.01)
*A61N 1/04*     (2006.01)
(52) U.S. Cl.
CPC ........... *A61N 1/3968* (2013.01); *A61N 1/046* (2013.01); *A61N 1/3993* (2013.01)

(58) Field of Classification Search
CPC ........ A61N 1/39; A61N 1/046; A61N 1/3968; A61N 1/3993
USPC ............................................................. 607/7
See application file for complete search history.

(56) References Cited

U.S. PATENT DOCUMENTS

| | | | |
|---|---|---|---|
| 4,681,112 A * | 7/1987 | Jones et al. ........................ 607/5 |
| 4,705,044 A * | 11/1987 | Deluhery et al. ............. 607/142 |
| 4,779,630 A * | 10/1988 | Scharnberg et al. ......... 607/142 |
| 4,850,356 A * | 7/1989 | Heath ............................. 607/142 |
| 4,915,109 A * | 4/1990 | Daynes et al. .................... 607/2 |
| 5,148,805 A * | 9/1992 | Scharnberg ....................... 607/2 |
| 5,342,403 A | 8/1994 | Powers et al. |
| 5,441,520 A | 8/1995 | Olsen et al. |
| 5,705,044 A | 1/1998 | Washburn et al. |
| 5,713,925 A * | 2/1998 | Sullivan et al. .................. 607/4 |
| 5,713,927 A * | 2/1998 | Hampele et al. ................ 607/5 |

(Continued)

FOREIGN PATENT DOCUMENTS

GB    2460690 A    9/2009
JP    2004049566 A    2/2004
(Continued)

*Primary Examiner* — Christopher A Flory

(57) ABSTRACT

An improved user interface for a defibrillator (100) capable of being used with paddle electrodes (180) and adhesive pad electrodes (190). A shock delivery button (110) located on the defibrillator control panel delivers a shock through the pad electrodes. A second shock delivery button (210), located on the paddle electrodes, delivers a shock through the paddle electrodes. Both shock delivery buttons are configured with the same shape, operation and illumination in order to reduce user confusion.

9 Claims, 3 Drawing Sheets

(56) References Cited

U.S. PATENT DOCUMENTS

| | | | |
|---|---|---|---|
| 6,097,987 A | 8/2000 | Milani | |
| 6,266,562 B1* | 7/2001 | Leyde | 607/5 |
| 6,920,354 B2 | 7/2005 | Daynes et al. | |
| 7,510,526 B2* | 3/2009 | Merry et al. | 600/300 |
| 8,615,295 B2* | 12/2013 | Savage et al. | 607/5 |
| 2001/0027270 A1* | 10/2001 | Stratbucker | 600/382 |
| 2002/0138103 A1 | 9/2002 | Mulhauser et al. | |
| 2006/0142805 A1 | 6/2006 | Katzman et al. | |
| 2006/0149323 A1* | 7/2006 | Merry et al. | 607/5 |
| 2009/0054939 A1* | 2/2009 | Hansen et al. | 607/5 |
| 2009/0149894 A1* | 6/2009 | Merry et al. | 607/2 |
| 2009/0292213 A1* | 11/2009 | Ferren et al. | 600/481 |
| 2010/0063559 A1 | 3/2010 | McIntyre et al. | |
| 2010/0094365 A9* | 4/2010 | Walker et al. | 607/3 |
| 2010/0241181 A1 | 9/2010 | Savage et al. | |
| 2010/0324612 A1* | 12/2010 | Matos | 607/4 |
| 2012/0226130 A1* | 9/2012 | De Graff et al. | 600/393 |
| 2014/0005737 A1* | 1/2014 | Kozin et al. | 607/7 |
| 2014/0039593 A1* | 2/2014 | Savage et al. | 607/142 |
| 2014/0039594 A1* | 2/2014 | Savage et al. | 607/142 |
| 2014/0148739 A1* | 5/2014 | Nour | 601/41 |

FOREIGN PATENT DOCUMENTS

| | | |
|---|---|---|
| JP | 2010509006 A | 3/2010 |
| WO | 02074387 A2 | 9/2002 |

\* cited by examiner

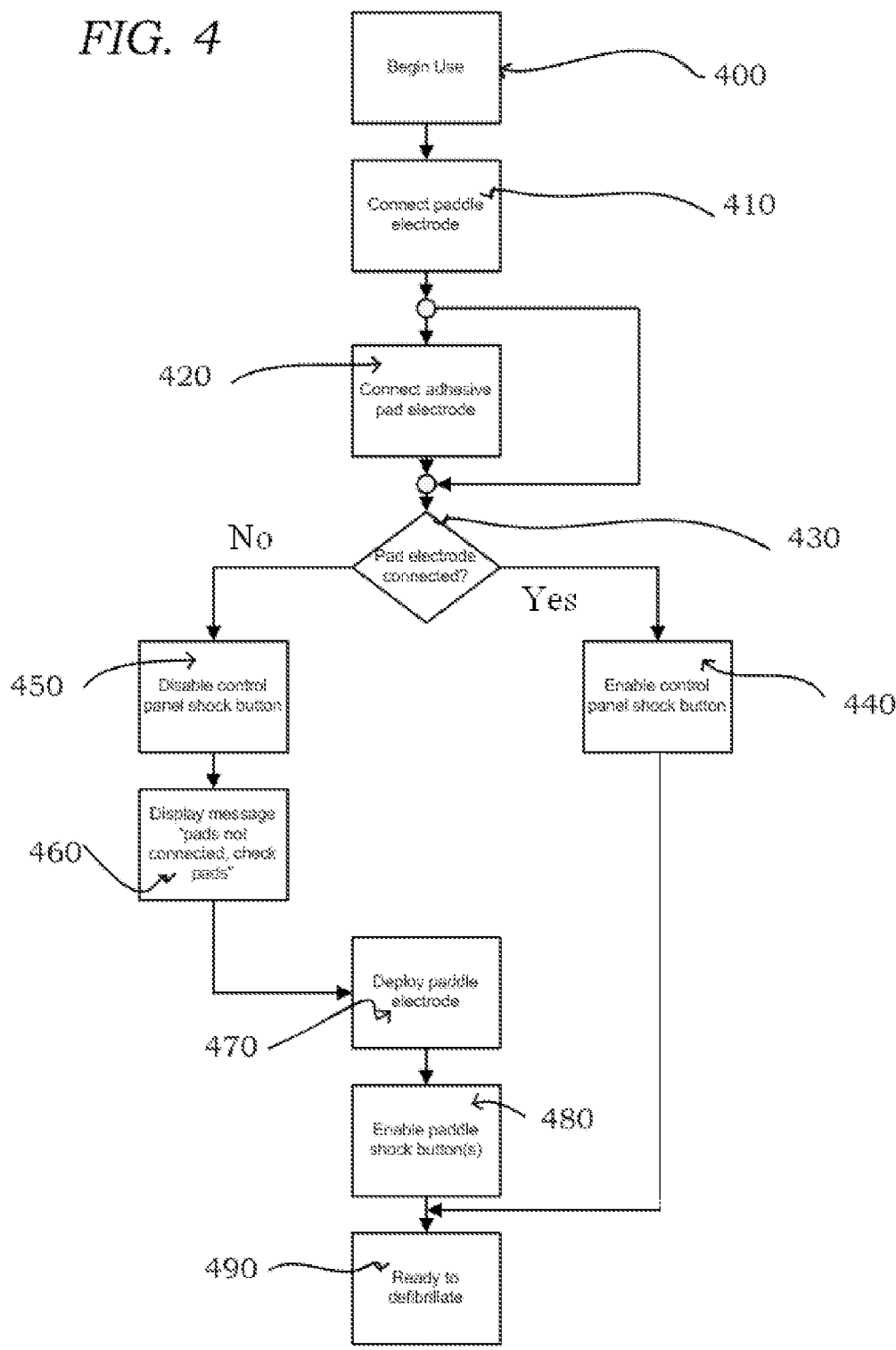

DEFIBRILLATOR PADDLES WITH LIGHTED SHOCK BUTTONS

The present invention relates to defibrillators for cardiac resuscitation. The invention relates in particular to an improved user interface for delivering defibrillation therapy from a defibrillator configured for electrodes both in a handheld paddle form and in an adhesively applied electrode pads form.

Cardiac arrest is a life-threatening medical condition in which the patient's heart fails to provide blood flow to support life. A defibrillator can be used to deliver defibrillating shocks to a patient suffering from cardiac arrest or other arrhythmia. The defibrillator resolves this condition by delivering a high-voltage impulse to the heart in order to restore normal rhythm and contractile function in patients who are experiencing cardiac arrhythmia.

Ventricular fibrillation (VF) or ventricular tachycardia (VT) are immediately life-threatening arrhythmias that are typically non-perfusing, i.e. not accompanied by spontaneous circulation. Atrial fibrillation (AF) is an arrhythmia which is potentially life-threatening, but is accompanied by spontaneous circulation. Each type of arrhythmia may be best treated with a different type of defibrillation shock. For example, AF is treated with a synchronized shock (cardioversion). VF and unstable VT are treated with an unsynchronized shock.

Defibrillators suitable for use in advanced life support or hospital environments often have a number of modes of operation. Each mode treats a different kind of cardiac event. Each event in turn has a different level of urgency in providing treatment. Advanced defibrillators such as these are typically more complicated to use.

For example, defibrillation of non-perfusing arrhythmias such as VF or VT must be delivered very soon after the onset of cardiac arrest in order to be effective. It is estimated that the chance of survival falls by 10% for every minute of delay to defibrillation beyond four minutes after cardiac arrest. Hence, it is vital that once a defibrillator is brought to the patient, the rescuer deploy and use it quickly.

Automated external defibrillator (AED) mode is effective for rapid treatment of non-perfusing arrhythmias by lesser-trained rescuers. In the AED mode, the defibrillator automatically analyzes the electrocardiogram (ECG) rhythm of an unconscious patient to quickly ascertain whether defibrillation is necessary. The defibrillator analyzes the ECG signal for signs of arrhythmia. If VF is detected, the defibrillator signals the rescuer that a shock is advised and charges its electrotherapy circuit to a therapeutic energy. The rescuer must only press a shock button on the defibrillator to deliver a defibrillation pulse to resuscitate the patient.

In the manual mode of operation, the defibrillator allows the user to select a desired amount of defibrillation energy and apply that energy directly to the patient without previous automatic diagnosis. Generally, only the minimum amount of energy necessary to convert the particular arrhythmia is desired, because too much energy can potentially injure the heart or create other complications. The user typically selects the energy level by turning a knob on the defibrillator control panel to one of several energy setting positions. The manual mode requires a more highly trained user to diagnose the underlying rhythm and select the proper therapeutic energy.

External defibrillators typically act through hand-held electrode paddles or adhesively-applied electrode pads applied across the chest of the patient. The electrodes are used to apply the defibrillating shock and can also be used to acquire an ECG signal from the patient's heart. Paddle electrodes typically have a shock delivery button(s) or key(s) located on the paddles themselves. The rescuer delivers the shock by pressing the paddles to the patient's torso, verifying that bystanders are clear, and then pressing the paddle shock key(s).

Defibrillators may also employ disposable adhesive electrodes, which are applied to the patient's torso. Defibrillators using these types of electrodes typically rely on a shock delivery button that resides on the defibrillator's front control panel. One exemplary defibrillator is the MRx monitor/Defibrillator, manufactured by Philips Electronics North America Corp. of Andover, Mass. which uses an orange triangular shaped shock button that is located on the front panel. The MRx shock button lights up when the device is ready to deliver a shock. FIG. 1 illustrates the front panel shock button 110 and the paddle shock button 120, 120' as disposed on the MRx monitor/defibrillator.

Many advanced defibrillators accept both paddle and adhesive electrodes. Therefore, a user may have one or more choices of shock delivery control depending on the electrode type employed.

A problem that arises with advanced defibrillators is that their complexity requires more training to use properly and efficiently. Many rescuers, such as first responders, are trained only in the use of simpler and more automated AEDs, which use adhesive electrodes. These rescuers may find themselves in situations in which only an advanced defibrillator having paddles is available. Any confusion or mistake associated with the rescuer's lack of familiarity with the device can lead to unacceptable delay of treatment.

Specifically, there is the possibility with existing advanced defibrillators that users unfamiliar with the complexity of the defibrillator may become confused by the differences between the appearance of the defibrillation control buttons on the front panel of the device and of the control buttons on the external paddles. The less-experienced user may delay treatment if he believes that the therapy differs according to differences in the control buttons. Thus it is desirable for an advanced defibrillator to have an intuitive user interface that a lesser-trained rescuer can quickly and unambiguously understand, deploy, and use.

The present invention arises from the discovery that the prior art arrangement of controls for delivering electrotherapy in an advanced defibrillator is not optimal. The inventors have discovered that the prior art arrangement may incur delay to defibrillation in a sudden cardiac arrest event because the operator may become confused by the differences between the user controls when using paddle-type electrodes or adhesive pad electrodes. The inventors have solved the problem by describing user controls that are consistent in shape and appearance across both types of electrodes.

In accordance with the principles of the present invention, a defibrillator for use with both paddle and adhesive electrodes is described, wherein the shock button or buttons on the paddles are configured to visually match the orange triangular shock button on the front panel of the defibrillator. Thus, the overall user interface is conformed and simplified, which reduces confusion during use.

In accordance with another embodiment of the present invention, a defibrillator for use with both paddle and adhesive electrodes is described, wherein the shock button or buttons on the paddles are configured to selectively light up when the product is charged and ready to shock. The shock button on the paddle electrode operates and looks similar to the shock button located on the control panel. This feature reduces confusion, by intuitively informing lesser-trained users that the paddle shock button or buttons initiate exactly the same therapy as the shock button on the front panel.

In accordance with yet another embodiment of the present invention, a defibrillator for use with both paddle and adhesive pad electrodes is described, wherein the control buttons and indications associated with charging and discharging the defibrillating high energy circuit have the same operation and appearance regardless of the type of electrodes in use.

In accordance with another embodiment of the present invention, a method of enabling a defibrillator for delivering therapy is described, comprising the steps of providing a first shock delivery button on a user control panel disposed on the defibrillator, electrically coupling either a paddle electrode having a second shock delivery button or an adhesive electrode to the defibrillator, sensing the coupling of the adhesive electrode and enabling the first shock delivery button only upon sensing the electrically coupling the adhesive electrode step. In this method, each of the first shock delivery button and the second shock delivery button has the same shape.

In the drawings:

FIG. 4 is a flow chart showing an improved method for delivering defibrillation shocks from a defibrillator having either a paddle or adhesive pad electrode.

DETAILED DESCRIPTION OF THE INVENTION

Figure 1:
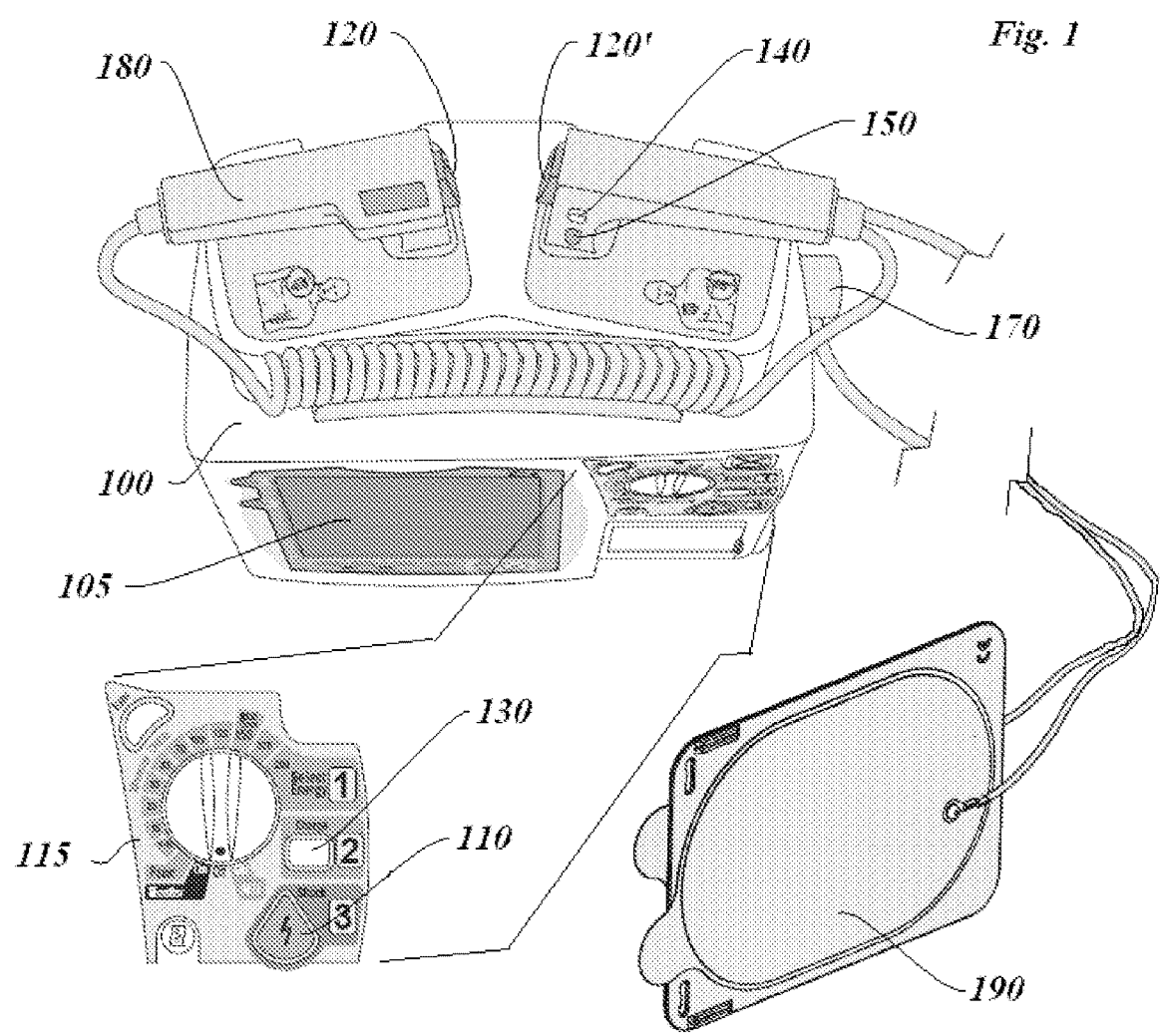
FIG. 1 illustrates a prior art defibrillator arrangement of shock control buttons for delivering electrotherapy through paddle or adhesive pad electrodes.

Turning now to FIG. 1, a known defibrillator 100 which is configured to use both a paddle electrode 180 or an adhesive pad electrode 190 is illustrated. The base of defibrillator 100 comprises a connector port 170 for electrodes and a user control panel 115. Messages regarding the status of the defibrillator, patient, and/or electrodes may be displayed on optional display 105.

User control panel 115 comprises graphic and text labeling indicia that are located adjacent to the controls associated with charging and discharging the defibrillating high energy circuit. FIG. 1 illustrates the use of text indications located next to the respective control, such as "Select Energy", "Charge", or "Shock." Alternatively, a 1-2-3 numbering scheme may be shown on user control panel 115 to help guide the user in the proper execution of the steps of a rescue. Thus, the first step of selecting energy may be indicated by a "1" label, the second step of charging the high energy circuit may be indicated by a "2" label, and the third step of delivering the shock may be indicated by a "3" label, each appearing adjacent the respective control.

Either type of electrode 180, 190 may be connected to defibrillator 100 at connector port 170. Alternatively, each type of electrode 180,190 may have a unique connector port on the defibrillator. Paddle electrodes 180 are employed by pressing the electrodes to the patient's chest at the standard anterior-anterior (A-A) positions. The defibrillator high energy circuit is charged by pressing charge button 140. When the defibrillator is fully charged and ready to shock, charge indicator light 150 illuminates. Aural or verbal prompts, such as "press shock button now", or "deliver shock now" may be issued simultaneously with the indicator light 150 illumination. Then, when good electrical contact with the patient is established, the user presses both shock buttons 120, 120' simultaneously to deliver the therapy.

Adhesive pad electrodes 190 are employed by applying the adhesive pads 190 to the patient's chest at either the A-A or anterior-posterior (A-P) positions. All shock controls for these pads are located on the control panel 115. The manual shock mode requires the user to press the charge button 130 on control panel 115 to charge the defibrillator high energy circuit. When the defibrillator is fully charged and ready to shock, shock button 110 illuminates. Aural or verbal prompts, such as "press shock button now", or "deliver shock now" may be issued simultaneously with the shock button 110 illumination. The user then presses shock button 110 to deliver the therapy.

Figure 2:
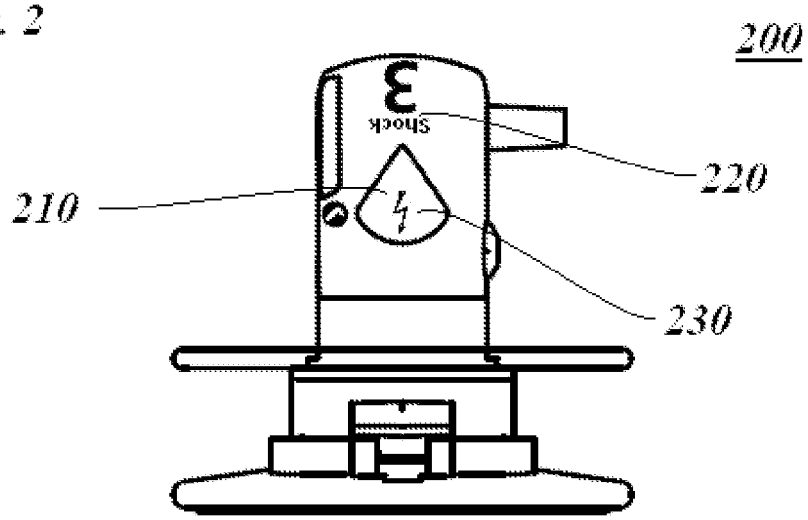
FIG. 2 illustrates an improved arrangement for a defibrillator shock button or buttons, as disposed on a paddle electrode.

FIG. 2 illustrates a paddle electrode 200 for a defibrillator, such as that shown in FIG. 1, having an improved shock button 210. The FIG. 2 embodiment adopts shock button 210 having the same appearance and operation as the shock button on the user control panel of the defibrillator to which the paddle is connected. In a preferred embodiment, shock button 210 has the same triangular or teardrop shape as shock button 110. Like shock button 110, shock button 210 includes a shock graphic 230 on the button, such as a lightning bolt graphic. The paddle 200 may also include a label 220, such as "Shock" or "3", that is similar to the indicia adjacent shock button 110 on the user control panel 115.

Shock button 210 may have the same color as the user control panel shock button; preferably red or orange. Shock button 210 may also incorporate the same internal illumination like the user control panel shock button. Shock button 210 would thus light up when the defibrillator high energy circuit is charged and armed for use. The lighted buttons may optionally flash when armed.

Shock button 220 should mimic the operation of the user control panel shock button as closely as possible. Each button may employ the same push button operation with tactile feedback when the internal switch closes. Each button may be comprised of the same outer textural material, such as silicon rubber. Within the exigencies of paddle operation ergonomics, the closing travel distance may be similar in each button.

Although just one paddle is shown in FIG. 2, it is understood that the improved shock button 210 may also be used on the second paddle as well. Thus, the improved shock button 210 may effectively replace both prior art shock buttons 120, 120' as shown in FIG. 1. If defibrillation paddle electrodes are in use, a shock is delivered by pressing both paddle shock buttons 210 simultaneously, as with the prior art paddle electrodes.

Figure 3:
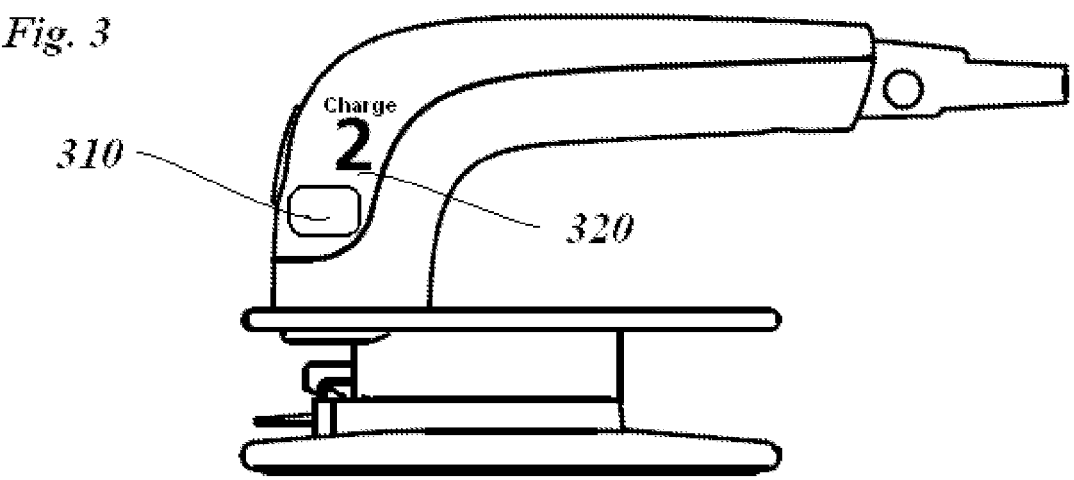
FIG. 3 illustrates an improved arrangement for a defibrillator charge control button, as disposed on a paddle electrode.

Turning now to FIG. 3, a paddle electrode 205 having an improved charging button 310 is illustrated. Under the same principles of invention as described above, the appearance and operation of the paddle charging button 310 is similar to the charging button that is located on the defibrillator user control panel. It is seen that charging button 310 effectively replaces both charge button 140 and charge indicator light 150 of the prior art paddle electrode 180. Although charging buttons 140, 310 are shown in FIGS. 1 and 3 to be rectangular, alternative shapes such as circular may be used.

Paddle electrode 205 may also include a label 320 next to the charging button 310 that is similar to the indicia adjacent charge button 130 on the user control panel 115. Such consistent labeling may be textual, such as the same word "Charge" or "2" appearing beside each charge button 310, 130. Charging button 310 may have the same color as the user control panel charge button; preferably blue or yellow. Charging button 310 may also incorporate the same internal illumination as the user control panel charging button. Shock button 210 would thus light up when the defibrillator high energy circuit is available to be charged.

It is understood that the shock delivery button 210, as well as the shock delivery button on the user control panel, differs in shape and appearance from any of the other non-shock delivery buttons employed by the defibrillator. In addition, the color and/or illumination of shock delivery button 210 is distinctive from any of the other non-shock delivery buttons employed by the defibrillator. These features further reduce operator confusion and more quickly direct the operator's attention to the controls required to deliver defibrillation therapy.

In order to reduce confusion further, defibrillator 110 may comprise a controller in communication with an electrode type sensor, which detects which of paddle electrode 200, 205 or adhesive electrode 190 is connected at connector port 170. If the electrode type sensor detects an adhesive pad electrode, the controller causes the shock delivery button on the user control panel to be enabled. In this case, the defibrillator may alert the user by button illumination, display 105 messaging, or aural indicators that the adhesive pad electrodes are connected and that the user control panel shock button is enabled.

Defibrillator 110 may further comprise a paddle electrode sensor disposed adjacent a paddle electrode holder that is attached to the base unit. The paddle electrode sensor detects when the paddle electrodes are removed from the holder, presumably for use. The paddle electrode sensor communicates paddle deployment to the controller, which then enables the paddle operating controls, i.e., the shock button and/or the charging button. If the controller senses both the connection of paddle electrodes and deployment of paddle electrodes, it may optionally disable the user control panel shock button. In this case, the defibrillator may alert the user by button illumination, display 105 messaging, or aural indicators that the paddle electrodes are connected and that the paddle shock button is enabled.

Turning now to FIG. 4, a method of enabling a defibrillator having either paddle electrodes or adhesive pad electrodes is illustrated. Use of the defibrillator begins at step 400. In addition, advanced defibrillators are typically staged with the paddle electrode already connected to the device, in order to allow rapid deployment. Thus, step 410 can also be accomplished before a defibrillation event begins.

At the beginning of the defibrillation event, a user may connect or replace the paddle electrode with an adhesive pad electrode, at step 420. Once the defibrillator is activated, its controller/sensor detects which type of electrode is in use at step 430. If the adhesive pad electrode is connected, the user control panel shock button is enabled, step 440. If the paddle electrode is connected, or if no electrode at all is detected, the controller may disable the user control panel shock button at step 450. The defibrillator may then display a message, warning light, or audible signal at step 460 that the electrode is not connected and to check the electrode.

If the paddle electrodes are connected, the defibrillator next senses when the paddle electrodes are removed from their holder for deployment at step 470. Once deployed, the defibrillator will enable the paddle electrode charging and shock controls, at step 480. Once either step 440 or step 480 is complete, the defibrillator is ready to deliver therapy, step 490.

The defibrillation method continues after step 490 similar to that performed in the prior art. When defibrillation is desired, the user presses the charge button on the front panel or paddle electrode. The defibrillator alerts the user when charging is complete. The user then applies the defibrillation therapy by pressing the enabled shock button on the paddle or user control panel as appropriate.

Other variations within the scope of the aforedescribed invention will readily occur to those skilled in the art. For instance, the particular identifying markings on the first and second shock buttons or the functionality of the underlying modes of enabling the buttons to deliver a shock may vary within the scope of the claimed invention.

The invention claimed is:

1. A defibrillator (100) configured to use both of a paddle electrode and an adhesive electrode (190), comprising:
   a base unit with a user control panel (115);
   a first shock delivery button (110) having a first shape disposed on the user control panel;
   a paddle electrode (200) electrically connected to the base unit;
   a second shock delivery button (210) having the first shape disposed on the paddle electrode; and
   a plurality of non-shock delivery buttons having a plurality of shapes,
   and further wherein the first shape is different than any other of the plurality of shapes.

2. The defibrillator of claim 1, wherein the first shape is one of a triangular shape or a teardrop shape.

3. The defibrillator of claim 1, wherein the first shock delivery button is illuminated in a first color when enabled for shock delivery, and further wherein the second shock delivery button is illuminated in the first color when enabled for shock delivery.

4. The defibrillator of claim 3, wherein the first shock delivery button flashes when enabled, and wherein the second shock delivery button flashes when enabled.

5. The defibrillator of claim 4, wherein the plurality of non-shock delivery buttons have a plurality of colors that are different than the first color.

6. The defibrillator of claim 1, further comprising:
   an electrode type sensor for sensing when the adhesive electrode is connected; and
   a controller communicatively coupled to the electrode type sensor and to the first shock delivery button, wherein the controller enables the first shock delivery button if the electrode type sensor detects that the adhesive electrode is connected.

7. The defibrillator of claim 6, wherein the first shock delivery button is illuminated when the adhesive electrode is connected.

8. The defibrillator of claim 1, further comprising:
   a paddle holder disposed on the base unit for holding the paddle electrode;
   a paddle sensor for sensing when the paddle electrode is removed from the paddle holder; and
   a controller communicatively coupled to the paddle sensor and to the second shock delivery button, wherein the controller enables the second shock delivery button when the paddle electrode is deployed.

9. The defibrillator of claim 1, further comprising:
   a second paddle electrode electrically connected to the base unit; and a third shock delivery button having the first shape disposed on the second paddle electrode.

\* \* \* \* \*